United States Patent [19]

Rufer et al.

[11] Patent Number: 4,555,406
[45] Date of Patent: Nov. 26, 1985

[54] INDANYL DERIVATIVES, THEIR PREPARATION AND USE

[75] Inventors: Clemens Rufer, Berlin, Fed. Rep. of Germany; Irmgard Boettcher, Basel, Switzerland

[73] Assignee: Schering Aktiengesellschaft, Berlin and Bergkamen, Fed. Rep. of Germany

[21] Appl. No.: 529,629

[22] Filed: Sep. 6, 1983

[51] Int. Cl.⁴ .................... A61K 31/18; C07C 143/75
[52] U.S. Cl. .................................................. 514/605
[58] Field of Search .......................... 564/99; 424/321

[56] References Cited

U.S. PATENT DOCUMENTS 4,244,960  1/1981  Schröder et al. .................. 424/263
4,375,479  3/1983  Schroeder et al. ................. 424/321

FOREIGN PATENT DOCUMENTS 3208079  9/1983  Fed. Rep. of Germany ........ 564/99

Primary Examiner—Paul F. Shaver
Attorney, Agent, or Firm—Millen & White

[57] ABSTRACT

An indanyl derivative of the formula

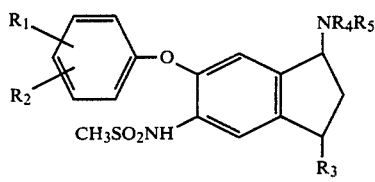

wherein
$R_1$ and $R_2$ are identical or different, and each is hydrogen, fluorine or chlorine
$R_3$ is hydrogen of phenyl
$R_4$ is hydrogen or alkyl of 1-6 carbon atoms, and
$R_5$ is hydrogen, alkyl of 1-6 carbon atoms, cyclohexyl or phenyl
with the proviso that at least one of the substituents $R_3$, $R_4$, and $R_5$ is different from hydrogen, or physiologically acceptable salts thereof with an acid,
have valuable pharmacological properties.

20 Claims, No Drawings

INDANYL DERIVATIVES, THEIR PREPARATION AND USE

The present invention relates to novel indanyl derivatives, a process for their preparation and pharmaceutical preparations containing them as an active ingredient.

SUMMARY OF THE INVENTION

It is an object of this invention to provide new compounds having pharmacological properties.

Upon further study of the specification and appended claims, further objects and advantages of this invention will become apparent to those skilled in the art.

These objects have been attained by providing indanyl derivatives of formula I

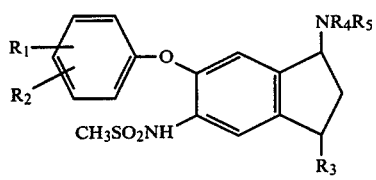

wherein
$R_1$ and $R_2$ are identical or different, and each is hydrogen, fluorine, or chlorine
$R_3$ is hydrogen or phenyl
$R_4$ is hydrogen or alkyl of 1-6 carbon atoms, and
$R_5$ is hydrogen, alkyl of 1-6 carbon atoms, cyclohexyl or phenyl
with the proviso that at least one of the substituents $R_3$, $R_4$, and $R_5$ is different from hydrogen, or a physiologically acceptable salt thereof with an acid.

DETAILED DISCUSSION

The substituents $R_1$ and $R_2$ of the indanyl derivatives can be identical or different. Preferably, $R_1$ and $R_2$ represent o,p-difluoro; $R_3$ is H; $R_4$ is H; and/or $R_5$ is alkyl.

The novel indanyl derivatives of Formula I can be produced according to known processes. Suitable manufacturing methods include, for example, the process described in "Methoden der Organischen Chemie" [Methods of Organic Chemistry] (Houben-Weyl) vol. XI/1, 4th ed. (1957), pp. 24 et seq., 217 et seq., and 341 et seq., whose disclosures are incorporated by reference herein.

Thus, a process for the preparation of the indanyl derivatives of Formula I comprises, (a) conventionally condensing an indan derivative of Formula II

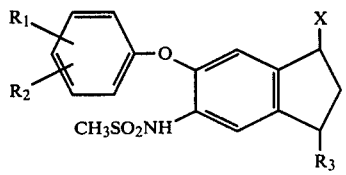

wherein
$R_1$, $R_2$ and $R_3$ are as defined above, and
X is chlorine, bromine or arylsulfonyl (especially p-toluenesulfonyl), with an amine of Formula III

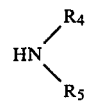

wherein $R_4$ and $R_5$ are as defined above; or
(b) conventionally hydrogenating an indan derivative of Formula IV

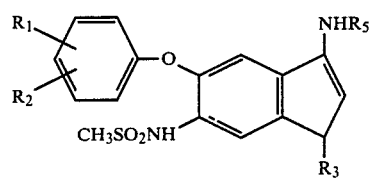

and optionally, conventionally converting the thus-obtained indan derivatives into the salts thereof.

The starting compounds for the above processes of this invention are known or can be produced by fully conventional methods. See, e.g., U.S. Pat. No. 4,244,960 in this regard and also relating to the above preparations themselves. The disclosure of U.S. Pat. No. 4,244,960 is entirely incorporated by reference herein.

The compounds of this invention are distinguished by a good antiphlogistic activity. Moreover, the compounds of this invention excel in view of their analgesic, antidysmenorrheic, antipyretic, thrombocyte-aggregation-inhibiting, and diuretic activity. It is, furthermore, significant that these compounds hardly impede prostaglandin synthesis. A special advantage of these compounds is their high dissociation between therapeutic effectiveness and undesired side effects (especially ulcerogenesis).

Consequently, the novel compounds are suitable, in combination with the excipients customary in galenic pharmacy, for the treatment of diseases of the rheumatoid array of disorders (such as rheumatoid arthritis, osteoarthritis, or ankylosing spondylitis), bronchial asthma, hay fever, etc.

It is furthermore remarkable that the indanyl derivatives of this invention also lend themselves to the treatment of migraine and dysmenorrhea and reduce the risk of thrombosis.

Surprisingly, among the indanyl derivatives of this invention are also those possessing additionally a pronounced antiulcerogenic as well as tumor-inhibiting efficacy.

The special medical preparations are produced as usual by converting the active compounds together with suitable additives, excipients, and flavoring agents into the desired forms of administration, such as tablets, dragees, capsules, solutions, inhalants, etc.

For parenteral application, particularly suitable are injectable sterile solutions, perferably oily or aqueous solutions, as well as suspensions, emulsions, or implants, including suppositories. Ampoules are convenient unit dosages.

Especially suitable for oral administration are tablets, dragees, and capsules containing, for example, 1-250 mg of active ingredient and 50 mg to 2 g of a pharmacologically inert vehicle, such as, for example, lactose, amylose, talc, gelatin, magnesium stearate, and similar agents, as well as the customary additives.

Conventional excipients are pharmaceutically acceptable organic or inorganic carrier substances suitable for parenteral, enteral or topical application to mammals, including humans, which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the compounds.

Typically, the compounds of this invention are administered in full analogy to the administration of the known antiinflammatory indomethacin.

Dosages for a given host for a given indication can be determined, e.g., by customary comparison of the activities of the subject compound and of a known agent by means of an appropriate, conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A suspension of 3.53 g of 6-(2,4-difluorophenoxy)-5-methylsulfonylamino-1-indanone in 40 ml of methanol is combined with 2 g of methylamine. The thus-produced solution is stirred for 2½ hours, and then 600 mg of palladium-charcoal (10%) is added thereto. The mixture is hydrogenated under normal pressure. After removing the catalyst by filtration, the product is concentrated and recrystallized from a mixture of ethanol-aqueous hydrochloric acid, thus obtaining 2.90 g of N-[6-(2,4-difluorophenoxy)-1-methylamino-5-indanyl]-methanesulfonamide, hydrochloride, mp 221° C.

The following compounds were prepared analogously to Example 1:

EXAMPLE 2

N-[6-(2,4-Difluorophenoxy)-1-ethylamino-5-indanyl]methanesulfonamide, hydrochloride, mp 216° C.

EXAMPLE 3

N-[6-(3-Chlorophenoxy)-1-ethylamino-5-indanyl]methanesulfonamide, hydrochloride, mp 210° C.

EXAMPLE 4

N-[6-(2,4-Difluorophenoxy)-1-propylamino-5-indanyl]methanesulfonamide, hydrochloride, mp 210° C.

EXAMPLE 5

N-(6-Phenoxy-1-propylamino-5-indanyl)methanesulfonamide, hydrochloride, mp 197° C.

EXAMPLE 6

N-[1-Cyclohexylamino-6-(2,4-difluorophenoxy)-5-indanyl]methanesulfonamide, hydrochloride, mp 221° C.

EXAMPLE 7

N-[1-Anilino-6-(2,4-difluorophenoxy)-5-indanyl]methanesulfonamide, mp 129° C. In this case, the mixture was concentrated after removing the catalyst by filtration and chromatographed with toluene over silica gel.

EXAMPLE 8

N-[6-(2,4-Difluorophenoxy)-3-phenyl-1-propylamino-5-indanyl]methanesulfonamide, mp 127° C.

6-(2,4-Difluorophenoxy)-5-methylsulfonylamino-3-phenyl-1-indanone, required for producing this compound, is obtained as follows:

120 g of 6-(2,4-difluorophenoxy)-5-indanylamine is kept in 1.2 l of acetic acid and 0.5 l of acetic anhydride for 30 minutes at 50° C. and then, at this temperature, a solution of chromium trioxide (110 g) in 50 ml of water and 300 ml of acetic acid is added dropwise thereto. After 30 minutes at 50° C., the mixture is concentrated, water is added, the mixture is extracted with chloroform and chromatographed with chloroform over a silica gel column, yielding 30 g of 6-acetylamino-5-(2,4-difluorophenoxy)-1indanone, mp 210° C. This quantity is dissolved in 500 ml of tetrahydrofuran, and the solution is combined at 40° C. with a phenylmagnesium bromide solution in ether (prepared from 24 g of magnesium, 108 ml of bromobenzene, and 500 ml of ether). After 16 hours at 20° C., the mixture is decomposed with ammonium chloride solution. The organic phase is stirred for 5 minutes with 8 g of p-toluenesulfonic acid. After filtration, the mixture is concentrated, the residue is extracted by stirring with petroleum ether and recrystallized from ethanol, thus obtaining 22 g of N-[6-(2,4-difluorophenoxy)-3-phenyl-5-indenyl]acetamide. This product is dissolved in 60 ml of dioxane and 240 ml of ethanol and hydrogenated over 1.2 g of palladium-charcoal (10%). Concentration and crystallization from petroleum ether yield 16.5 g of N-[6-(2,4-difluorophenoxy)-3-phenyl-5-indanyl]acetamide, mp 117° C. This product is stirred in 200 ml of acetone with a solution of 8 g of chromium trioxide, 20 ml of sulfuric acid, and 40 ml of acetic acid for 16 hours at 20° C. After adding sodium bisulfite, the mixture is concentrated, taken up in chloroform, the chloroform solution is washed with sodium hydroxide solution and concentrated. Chromatography over silica gel with toluene-ethyl acetate yields 6 g of 5-acetylamino-6-(2,4-difluorophenoxy)-3-phenyl-1-indanone, mp 163° C. This quantity is refluxed in 50 ml of ethanol and 10 ml of hydrochloric acid (10-normal) for 2 hours. After concentration, the mixture is made weakly alkaline with ammonia, vacuum-filtered, dried, taken up in 60 ml of pyridine, and combined with 2.3 g of methanesulfonyl chloride. The mixture is concentrated after having been left for 25 hours at 20° C., combined with water, vacuum-filtered, dissolved in 1N sodium hydroxide solution, and acidified with 10N hydrochloric acid. Vacuum-filtering yields 3.1 g of 6-(2,4-difluorophenoxy)-5-methylsulfonylamino-3-phenyl-1-indanone, mp 101° C.

EXAMPLE 9

2.84 g of N-[6-(2,4-difluorophenoxy)-1-hydroxy-5-indanyl]methanesulfonamide and 1.83 g of phosphorus pentachloride are stirred in 50 ml of dichloromethane-diethyl ether (1:1) for 45 minutes at 0° C. At 0° C., a solution of 7 g of dimethylamine in 25 ml of dichloromethane is added to the reaction mixture. After 2 hours at 20° C. and 20 minutes of boiling, the mixture is concentrated and the residue is recrystallized from aqueous hydrochloric acid, yielding 2.41 g of N-[6-(2,4-difluorophenoxy)-1-dimethylamino-5-indanyl]methanesulfonamide, hydrochloride, mp 195° C.

The following compound was prepared analogously to Example 9:

EXAMPLE 10

N-[6-(2,4-Difluorophenoxy)-1-dipropylamino-3-phenyl-5-indanyl]methanesulfonamide, hydrochloride, mp 167° C.

N-[6-(2,4-Difluorophenoxy)-1-hydroxy-3-phenyl-5-indanyl]methanesulfonamide, required for producing this compound, is obtained as follows:

2.13 g of 6-(2,4-difluorophenoxy)-5-methylsulfonylamino-3-phenyl-1-indanone is dissolved in 20 ml of methanol and 5.5 ml of 1N sodium hydroxide solution. At 0° C., 400 mg of sodium borohydride is added to the mixture. After 16 hours at 20° C., the mixture is concentrated, combined with water, neutralized with 1N sulfuric acid, and vacuum-filtered, thus obtaining 1.7 g of N-[6-(2,4-difluorophenoxy)1-hydroxy-5-indanyl]methanesulfonamide, mp 119° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An indanyl derivative of the formula

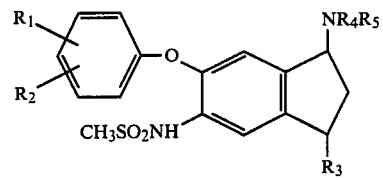

wherein
 $R_1$ and $R_2$ are identical or different, and each is hydrogen, flourine or chlorine
 $R_3$ is hydrogen or phenyl
 $R_4$ is hydrogen or alkyl of 1-6 carbon atoms, and
 $R_5$ is hydrogen, alkyl of 1-6 carbon atoms, cyclohexyl or phenyl
 with the proviso that at least one of the substituents $R_3$, $R_4$, and $R_5$ is different from hydrogen, or a physiologically acceptable salt thereof with an acid.

2. An indanyl derivative of claim 1, wherein $R_1$ and $R_2$ are o,p-difluoro.

3. An indanyl derivative of claim 1, wherein $R_3$ is hydrogen.

4. An indanyl derivative of claim 2, wherein $R_3$ is hydrogen.

5. An indanyl derivative of claim 1, wherein $R_4$ is hydrogen.

6. An indanyl derivative of claim 4, wherein $R_4$ is hydrogen.

7. An indanyl derivative of claim 1, wherein $R_5$ is alkyl.

8. An indanyl derivative of claim 6, wherein $R_5$ is alkyl.

9. N-[6-(2,4-Difluorophenoxy)-1-methylamino-5-indanyl]methanesulfonamide, a compound of claim 1.

10. N-[6-(2,4-Difluorophenoxy)-1-ethylamino-5-indanyl]methanesulfonamide, a compound of claim 1.

11. N-[6-(2,4-Difluorophenoxy)-1-propylamino-5-indanyl]methanesulfonamide, a compound of claim 1.

12. N-(6-Phenoxy-1-propylamino-5-indanyl)methanesulfonamide, a compound of claim 1.

13. N-[1-Cyclohexylamino-6-(2,4-difluorophenoxy)-5-indanyl]methanesulfonamide, a compound of claim 1.

14. N-[6-(2,4-Difluorophenoxy)-3-phenyl-1-propylamino-5-indanyl]methanesulfonamide, a compound of claim 1.

15. N-[6-(2,4-Difluorophenoxy)-1-dimethylamino-5-indanyl]methanesulfonamide, a compound of claim 1.

16. N-[6-(2,4-Difluorophenoxy)-1-dipropylamino-3-phenyl-5-indanyl]methanesulfonamide, a compound of claim 1.

17. N-[6-(3-Chlorophenoxy)-1-ethylamino-5-indanyl]methanesulfonamide, a compound of claim 1.

18. N-[1-Anilino-6-(2,4-difluorophenoxy)-5-indanyl]methanesulfonamide, a compound of claim 1.

19. A pharmaceutical composition comprising an antiphlogistically effective amount of a compound of claim 1 and a pharmaceutical carrier.

20. A method of treating inflammation in a patient in need of such treatment comprising administering to the patient an antiphlogistically effective amount of a compound of claim 1.

* * * * *